(12) United States Patent
Cohen et al.

(10) Patent No.: US 6,900,184 B2
(45) Date of Patent: May 31, 2005

(54) COMPOSITIONS CONTAINING PIPERCILLIN AND TAZOBACTAM USEFUL FOR INJECTION

(75) Inventors: Jonathan Marc Cohen, Monroe, NY (US); Syed M. Shah, Hanover, NJ (US); Christian Luther Ofslager, Newburgh, NY (US); Mahdi Fawzi, Morristown, NJ (US)

(73) Assignee: Wyeth Holdings Corporation, Madison, NJ (US)

(*) Notice: Subject to any disclaimer, the term of this patent is extended or adjusted under 35 U.S.C. 154(b) by 0 days.

(21) Appl. No.: 10/413,323

(22) Filed: Apr. 14, 2003

(65) Prior Publication Data

US 2004/0204372 A1 Oct. 14, 2004

(51) Int. Cl.$^7$ .................. A61K 31/70; A61K 31/43
(52) U.S. Cl. .................. 514/36; 514/41; 514/192
(58) Field of Search ............... 514/36, 41, 192

(56) References Cited

U.S. PATENT DOCUMENTS

| | | | |
|---|---|---|---|
| 4,477,452 A | 10/1984 | Haeger | |
| 4,534,977 A | 8/1985 | Haeger | |
| 4,562,073 A | 12/1985 | Micetich et al. | |
| 6,207,661 B1 | 3/2001 | Thompson et al. | |
| 2002/0035061 A1 | 3/2002 | Krieger et al. | |

FOREIGN PATENT DOCUMENTS

| | | | |
|---|---|---|---|
| WO | WO 00 50035 A | 8/2000 | |
| WO | WO 03 088914 A2 | 10/2003 | |

OTHER PUBLICATIONS

PCT Search Report, Dec. 12, 2003 (PCT/US03/11340).
L. Van Den Berg; D. Rose; Arch. Biochem. Biophys., 81, p. 319 (1959).
Remmington's Pharmaceutical Sciences, 18$^{th}$ Edition, A.R. Gennaro, Editor, Mack Publishing, 1990, p. 1567–1569.
Remmington's Pharmaceutical Sciences, 18$^{th}$ Edition, A.R. Gennaro, Editor, Mack Publishing, 1990, Chapter 84, p. 1565–1567.
Mathew, M., et al.; Journal of Clinical Pharmacy and Therapeutics, Jun. 19, 1994, pp. 397–399.
Park, T.W., et al., Am. J. Health–Syst. Pharm. 1995, 52 (Sep. 15), pp. 2022–2024.
Handbook of Pharmaceutical Excipients, Third Edition, Arthur H. Kibbe, Editor, 2000, pp. 482–484.
The United States Pharmacopeia, National Formulary, USP26, NF21, Jan. 1, 2003, pp. 1483–1485, pp. 2189–2196.
U.S. Pharmacopeia and National Formulary (1) Supplement, Apr. 1, 2003, pp. 2990–2991.
Zosyn® Package Insert, no date available.
R.C.Rowe and P.J. Sheskey; "Handbook of Pharmaceutical Excipients, third edition"; 2000, Pharmaceutical Press, Washington; pp. 191–194.
PCT Search Report Aug. 24, 2004 (PCT/US2004/010698).

Primary Examiner—Raymond J. Henley, III
(74) Attorney, Agent, or Firm—Daniel B. Moran

(57) ABSTRACT

The invention pertains to pharmaceutical compositions of Zosyn® piperacillin with tazobactam in the presence of a buffer, preferably citrate, a particulate formation inhibitor, preferably EDTA optionally an aminoglycoside which when frozen and thawed or lyophilized and reconstituted reform a solution which has decreased particulate formation.

90 Claims, No Drawings

COMPOSITIONS CONTAINING PIPERCILLIN AND TAZOBACTAM USEFUL FOR INJECTION

FIELD OF THE INVENTION

The invention relates to pharmaceutical compositions containing piperacillin (normally as piperacillin sodium) and tazobactam-(normally as tazobactam sodium) commercially available as Zosyn®. Such compositions are useful for intravenous administration as antibiotics for hospitalized patients with serious infections. Specifically, this invention relates to a pharmaceutical composition further including an aminocarboxylic acid chelating agent, for example, ethylene diamine tetraacetic acid (EDTA), or a pharmaceutically acceptable salt thereof, and optionally citrate and optionally an aminoglycoside. The pharmaceutical compositions described herein normally have enhanced resistance to particulate formation in solutions to be administered parenterally.

BACKGROUND OF THE INVENTION

Zosyn® is an antibiotic marketed product containing piperacillin sodium and tazobactam sodium. The product is disclosed in U.S. Pat. No. 4,562,073. U.S. Pat. Nos. 4,477,452 and 4,534,977 disclose a lyophilized form of piperacillin.

Zosyn® is an antibiotic which is used in the treatment of moderate to severe infections caused by piperacillin-resistant, piperacillin/tazobactam-susceptible beta-lactamase-producing strains of microorganisms in conditions such as nosocomial pneumonia due to *Staphylococcus aureus*; intra-abdominal infections, specifically appendicitis (complicated by rupture or abscess) and peritonitis due to *Escherichia coli*, skin and skin structure infections, including cellulitits, cutaneous abscesses and ischemic/diabetic foot infections due to *Staphylococcus aureus*; and gynecologic infections, specifically postpartum endometritis or pelvic inflammatory disease due to *Escherichia coli*. The seriousness of these infections highlights the need for a readily available and dependable treatment. Piperacillin is a broad-spectrum beta-lactam antibiotic which is inherently unstable in solution at room temperature. Adversely, instability in solution at room temperature further results in increased particulate formation.

Additionally, piperacillin is vulnerable to beta-lactamase enzymes. Tazobactam reduces the vulnerability of the piperacillin to the bacteria that produce beta-lactamase enzymes. Basically, the tazobactam permanently inactivates beta-lactamases, allowing the piperacillin component to destroy susceptible bacteria.

Polymicrobial infections often include pathogens that produce beta-lactamase enzymes. These enzymes commonly cause resistance to penicillins and cephalosporins. Without treatment these microbes would multiply and thrive unimpeded, with serious or critical consequences to the patient.

Medicaments are formulated into not only emulsions, suspensions or solutions, but also as lyophilized preparations to be reconstituted before use. Advantageously, lyophilized preparations are stable, can be stored and are easily reconstituted. Moreover lyophilized preparations may be kept sterile and essentially free of insoluble matter. However, when Zosyn® is reconstituted or a frozen bag is thawed particulate matter formation begins.

Zosyn® is available as a powder (lyophilized product) which is reconstituted by addition of a compatible reconstitution diluent prior to intravenous administration.

Zosyn® is also available as a liquid premix formulation containing piperacillin sodium, tazobactam sodium and sodium citrate as buffer. Such a formulation is disclosed in U.S. Pat. No. 6,207,661. This liquid premix is stored frozen and then parenterally administered to the patient after thawing and, if desired, adding a compatible diluent. The addition of citrate as buffer adjusts the pH to about 6.5.

In a hospital setting, aminoglycoside antibiotics may optionally be added to the frozen and thawed or reconstituted presentations. However, not without the disadvantage of particulate formation.

Zinc content of the reconstituted lyophilized product or frozen and thawed product optionally in the presence of aminoglycosides enhances the formation of particulates. The presence of zinc in IV solutions is known to arise from plastic storage containers, septa and tubing.

The amount of zinc in IV bags can vary from lot to lot even when manufactured by the same manufacturer. Typically, the hospitals would not analyze the bags prior to use and therefore will be unaware of what level of zinc is present.

Particulates are formed as reconstituted lyophilized formulations and thawed frozen formulations are readied and stored prior to patient administration. As the time increases from reconstitution or thawing and delivery to the patient so does formation of particulates. Storage after reconstitution or thawing also allows for the formation of unwanted particulates. It is recognized that the presence of particles in solution, particularly if injected intravenously, can be harmful. In particular, it has been shown that the development of infusion-phlebitis may be related to the presence of particulate matter in intravenous fluids (Remmington's Pharmaceutical Sciences, 18 edition, Mack Publishing, 1990. Page 1567).

The pharmaceutical compositions of the present invention overcome the disadvantages of pharmaceutical compositions known in the art. In particular, decreased particulate formations in pharmaceutical compositions upon reconstitution and thawing is solved by the present invention. Advantageously, pharmaceutical compositions of the invention which may optionally have an aminoglycoside also have decreased particulate formation.

Zosyn® has been found to be stable in glass and plastic containers (such as plastic syringes, and I.V. bags) when used with compatible diluents. Various studies of the stability of Zosyn® have been carried out. For example, Park T W et al. in Am J Health Syst Pharm; 1995; 52 (September 15); 2022–2024 studied the stability of Zosyn in 2 continuous ambulatory peritoneal dialysis (CAPD) solutions at 3 temperatures by adding 200 mg/ml solution of piperacillin sodium and 25 mg/ml of tazobactam sodium to 2 l bags of Dianeal PD-2 with 1.5% dextrose and 2 l bags of Dianeal PD-2 with 4.25% dextrose and storing the products at 4, 23 or 37° C., respectively. No precipitation or color change was observed at all study times. Piperacillin and tazobactam were found to be stable in 2 CAPD solutions for at least 1 day when stored at 37° C., 7 days at 23° C., and 14 days at 4° C. Mathew M et al. in J Clin Pharm Ther; 1994; 19 (Jun); 397–399 studied the stability of piperacillin sodium in the presence of tazobactam sodium in 5% dextrose and normal saline i.v. admixtures by using a modified stability-indicating high performance liquid chromatography assay method reported in the literature. The solutions were stored at room and refrigerator temperatures in plastic bags. They remained clear throughout the study. The solutions were stable for 2 days at 25° C. and for 28 days at 5° C.

Parenteral drug products should be inspected visually for particulate matter and discoloration prior to administration, whenever possible. Although existing Zosyn® formulations exhibit satisfactory clarity when prepared in accordance with recommended manufacturer's instructions, it is desirable to minimize the particulate formations that occur in the pharmaceutical compositions upon reconstitution and thawing. Surprisingly it has been found that incorporation of an aminocarboxylic acid chelating agent, for example, ethylene diamine tetraacetic acid (EDTA) or diethylenetriamine pentaacetic acid (DTPA), or a suitable salt thereof into the composition can generally be used to inhibit particulate formation.

BRIEF SUMMARY OF THE INVENTION

The present invention provides to the art a new pharmaceutical composition of premixed piperacillin or piperacillin-tazobactam which avoids the particulate formation of the prior art and is capable of being frozen and thawed and useful for the treatment or control of bacterial infections by parenteral administration, the composition comprising effective amounts of (a) piperacillin or a pharmaceutically acceptable salt thereof (normally as piperacillin sodium), (b) tazobactam or a pharmaceutically acceptable salt thereof (normally as tazobactam sodium), and, as particulate formation inhibitor, an aminocarboxylic acid chelating agent for example. ethylenediaminetetraacetic acid (EDTA), diethylenetriaminepentaacetic acid (DTPA), hydroxyethylenediaminetriacetic acid (HEDTA), nitrilotriacetic acid (NTA) or a pharmaceutically acceptable salt thereof (normally as a sodium salt). The pharmaceutical composition according to the invention may be (A) in the form of a powder that can be reconstituted by addition of a compatible reconstitution diluent prior to parenteral administration, (B) in a form ready to use for parenteral administration or (C) in a form ready to use for parenteral administration. The composition of the invention normally reduces the formation of particulates compared to the prior art.

Particulates consist of mobile, randomly sourced, extraneous substances, other than gas bubbles, that cannot be quantitated by chemical analysis due to the small amount of material that represents and to its heterogeneous composition.

In one embodiment of the present invention, an effective amount of tazobactam, as tazobactam sodium and piperacillin, as piperacillin sodium, is included in a buffered solution and further including an effective amount of a particulate formation inhibitor of the invention. The pH of this embodiment may be maintained within a range of about 6.0 to 7.5. The pH, and therefore the stability of the solution, can be maintained by buffering with, for instance, an effective amount of citrate.

Particulate formation inhibitors include ethylenediaminetetraacetic acid (EDTA) and salts thereof. Preferably, ethylenediaminetetraacetic acid (EDTA) is edetate disodium, (USP), where USP means United States Pharmacopia.

In still another embodiment, any of the previous embodiments may be made physiologically iso-osmotic (a.k.a., isosmotic, isotonic) with the addition of dextrose hydrous or dextrose anhydrous.

One embodiment of the present invention is to further optionally include aminoglycosides in pharmaceutical compositions described herein.

This invention includes a solid lyophilized composition suitable for making a liquid useful for treatment of bacterial infections in mammals which when reconstituted generally has reduced particulate formation.

This invention is also includes an aqueous solution of a reconstituted lyophilized composition useful for the treatment of bacterial infections in mammals.

This invention also includes a process of making a lyophilized composition and other compositions of the invention. The invention provides a process for the manufacture of a pharmaceutical composition useful for the treatment or control of bacterial infections preferably by parenteral administration, the pharmaceutical composition being in the form of a powder that can be reconstituted by addition of a compatible reconstitution diluent prior to parenteral administration or in the form of a frozen composition adapted to be thawed and, if desired, diluted with a compatible diluent prior to parenteral administration; which process comprises freezing or freeze-drying a solution containing effective amounts of (a) piperacillin or a pharmaceutically acceptable salt thereof, (b) tazobactam or a pharmaceutically acceptable salt thereof and, as particulate formation inhibitor, an aminocarboxylic acid chelating agent or a pharmaceutically acceptable salt thereof and optionally including an aminoglycoside antibiotic in an aqueous vehicle.

This invention also includes a method of treating bacterial infections in mammals using the composition of the invention.

This invention additionally includes an improved method of treating bacterial infections in mammals using the thawed composition of the invention.

This invention also includes a powder (lyophilized composition) dissolved in aqueous medium in a unit dosage IV bag or bottle at a concentration suitable for intravenous administration to a mammal for treatment of bacterial infections.

This invention further includes a powder (lyophilized composition) contained in a dose-concentrate sealed container.

A further aspect of this invention is a process for the preparation of a powder (lyophilized composition) and a process for the preparation of a liquid composition capable of being frozen and thawed.

Other advantages and aspects of the present invention will become apparent upon reading the following detailed description of the invention.

DESCRIPTION OF PREFERRED EMBODIMENTS

The present inventive compositions offer a number of advantages over other forms of piperacillin and piperacillin-tazobactam for administration. For example, the solution for infusion may demonstrate a reduction in both the quantity of particulates and the rate of their formation whether derived from a reconstituted lyophilized or frozen and thawed premixed dosage form. Inhibiting particular formation may be achieved by buffering the pharmaceutical compositions of the invention with a buffer, for example, citrate to maintain the suitable pH range of about 6.0 to about 7.5 and further adding an aminocarboxylic acid chelating agent or a salt thereof as particulate formation inhibitor to limit particulate formation. A preferred pH is about 6.5. Further shown in Table 1 the presence of EDTA in the form of edetate disodium dihydrate as the particulate formation inhibitor significantly reduces the number of particles generated in 24 hours. Optionally the particulate formation inhibitor may be added in a hospital setting before administration to a patient or may also be premixed in a ready to use pharmaceutical composition.

In an additional aspect of the invention, aminoglycosides may optionally be added to the pharmaceutical compositions of the invention. Further the aminoglycosides may optionally be admixed in a hospital setting by adding to the frozen bag on thawing or to the reconstituted lyophilized composition before administration to a patient or premixed in a lyophilized or frozen pharmaceutical composition. As shown in Table 1 the presence of the aminoglycoside amikacin increases the number of particles generated in 24 hours. However, the formation of particles is normally reduced in the presence of citrate and the particulate formation inhibitor EDTA in the form of edetate disodium dihydrate. Certain pharmaceutical compositions of the present invention are premixed so they are ready for immediate use upon thawing or reconstitution which eliminates the requirement to form after thawing or reconstitution an admixture with a particle formation inhibitor and optionally an aminoglycoside. While the particle formation inhibitor EDTA (or other aminocarboxylic chelating agent) may optionally be added to the thawed or reconstituted pharmaceutical composition, preferably premixing before freezing or lyophilization has the advantage of preventing the inadvertent adding of the incorrect reagent or amount to the composition and allows for easier administration to the patient.

Further, certain pharmaceutical compositions of the present invention are premixed so they are ready for immediate use upon thawing or reconstitution which eliminates the requirement to form after thawing or reconstitution an admixture with an aminoglycoside. While the aminoglycoside, may optionally be added to the thawed or reconstituted pharmaceutical composition, preferably premixing before freezing or lyophilization has the advantage of preventing the inadvertent adding of the incorrect reagent or amount to the composition and allows for easier administration to the patient.

The term, "dose-concentrate" refers to a solution of the pharmaceutical composition. The dose-concentrate may be held in the container where it was formed by adding aqueous solvent or diluent to the pharmaceutical composition or it may be removed and held externally. The dose-concentrate may be used as is, but is generally further diluted to a unit dosage concentration for administration to a mammal. The entire volume of the dose-concentrate or aliquots thereof may be used in preparing unit dose(s) for treatment by the method of this invention.

The term, "particulate formation inhibitor", refers to a compound which has the desired property of inhibiting the formation of particles in parenteral compositions containing piperacillin and tazobactam. Particulate formation inhibitors of the invention include ethylenediaminetetraacetic acid (EDTA) and salts thereof, for example, ethylenediaminetetraacetic acid, calcium disodium salt (preferably as the hydrate); ethylenediaminetetraacetic acid, diammonium salt (preferably as the hydrate); ethylenediaminetetraacetic acid, dipotassium salt (preferably as the dihydrate); ethylenediaminetetraacetic acid, disodium salt (preferably as the dihydrate and, if desired, as the anhydrous form); ethylenediaminetetraacetic acid, tetrasodium salt (preferably as the hydrate); ethylenediaminetetraacetic acid, tripotassium salt (preferably as the dihydrate); ethylenediaminetetraacetic acid, trisodium salt (preferably as the hydrate) and ethylenediaminetetraacetic acid disodium salt, USP(preferably as the dihydrate). Preferably, the pharmaceutical compositions described herein have an effective amount of a particulate formation inhibitor.

Ethylenediaminetetraacetic acid disodium salt, USP is the preferred form for the particulate formation inhibitors used in the present invention. The amount of particulate formation inhibitor such as ethylenediaminetetraacetic acid disodium salt USP is preferably within the range of about 0.01 to about 40 mg particulate formation inhibitor per gram of piperacillin, more preferably within the range of about 0.1 to about 0.5 mg particulate formation inhibitor per gram of piperacillin, or any range or subcombination of ranges therein.

Piperacillin sodium is the preferred form of piperacillin in the compositions of the present invention. Piperacillin free acid is the preferred source of piperacillin for use in making the compositions of the present invention. The free acid may be converted to the sodium salt during the formulation process. Piperacillin sodium is derived from D(−)-α-aminobenzylpenicillin. The chemical name of piperacillin sodium is sodium (2S, 5R, 6R)-6-[(R)-2-(4-ethyl-2,3-dioxo-1-piperazinecarboxamido)-2-phenylacetamido]-5 3,3-dimethyl-7-oxo-4-thia-1-azabicyclo(3.2.0) heptane-2-carboxylate, with a chemical formula of $C_{23}H_{26}N_5O_7SNa$ and a molecular weight of 539.6.

When making the frozen (ready for use upon thawing) dosage form, the piperacillin free acid is preferably mixed with a quantity of deionized water, and neutralized with sodium bicarbonate or other suitable agents, to bring the concentration of the solution within the preferred range of about 8 to about 90 mg/ml, more preferably within the range of about 25 to about 85 mg/ml, and most preferably within the range of about 30 to about 80 mg/ml or any combination or subcombination of ranges therein.

When making the lyophilized dosage forms (dry powder which needs reconstitution and dilution prior administration to a mammal), the piperacillin free acid is preferably mixed with a quantity of deionized water, and neutralized with sodium bicarbonate or other suitable agents, to bring the concentration of the solution within the preferred range of about 150 to about 500 mg/ml, more preferably within the range of about 200 to about 400 mg/ml, and most preferably within the range of about 220 to about 350 mg/ml or any combination or subcombination of ranges therein. Lower concentrations of solute can be processed successfully, but with the disadvantages of increasing production times and associated costs.

When a lyophilized dosage form is reconstituted and diluted for administration, the concentration of the piperacillin in solution is within the preferred range of about 8 to about 90 mg/ml, more preferably within the range of about 25 to about 85 mg/ml, and most preferably within the range of about 30 to about 80 mg/ml or any combination or subcombination of ranges therein.

Tazobactam sodium is the preferred form of tazobactam in the compositions of the present invention. Tazobactam free acid is the preferred source of tazobactam for use in making the compositions of the present invention. The free acid may be converted to the sodium salt during the process of forming the pharmaceutical compositions of the invention. Tazobactam sodium, a derivative of the penicillin nucleus, is a penicillanic acid sulfone. Its chemical name is sodium (2S, 3S, 5R)-3-methyl-7-oxo-3-(1H-1,2,3-triazol-1-ylmethyl)-4-thia-1-azabicyclo-(3,2,0)heptane-2-carboxylate-4,4-dioxide. The chemical formula for tazobactam sodium is $C_{10}H_{11}N_4NaO_5S$ and the molecular weight is 322.3. When making the frozen (ready for use upon thawing) dosage form, tazobactam free acid may be added to the piperacillin solution to create a concentration of tazobactam sodium to within a preferable range of about 0.1 to about 25 mg/ml, more preferably within the range of about 1.0 to about 22 mg/ml, and most preferably within the range of about 3 to about 20 mg/ml, or any range or subcombination of ranges therein.

When making the lyophilized dosage forms (dry powder which needs reconstitution and dilution prior administration to a mammal), tazobactam free acid may be to be added to the piperacillin solution to create a concentration of tazobactam sodium to within a preferable range of about 15 to about 125 mg/ml, more preferably within the range of about 2 to about 100 mg/ml, and most preferably within the range of about 27 to about 90 mg/ml, or any range or subcombination of ranges therein.

When a lyophilized pharmaceutical composition is reconstituted and diluted for administration, the concentration of tazobactam in the solution is within a preferable range of about 0.1 to about 25 mg/ml, more preferably within the range of about 1.0 to about 22 mg/ml, and most preferably within the range of about 3 to about 20 mg/ml, or any range or subcombination of ranges therein.

The total concentration of piperacillin sodium, tazobactam sodium, citrate as buffer and particulate formation inhibitor in solution when the dosage form is ready for patient use is preferably within the range of about 9 to about 125 mg/ml. More preferably the total concentration is within the range of about 14 to about 115 mg/ml, and most preferably within the range of about 20 to about 105 mg/ml, or any range or subcombination of ranges therein. These quantities allow for an effective amount of piperacillin or piperacillin/tazobactam to be delivered in common dosage amounts of about 50 to about 250 ml. A suitable pH range is about 6.0 to about 7.5. The resulting piperacillin or piperacillin/tazobactam solution may then be brought to within a preferred pH range of about 6.1 to about 6.9, and more preferably within the range of about 6.3 to about 6.7. In a preferred form of the invention the pH of the solution is about 6.5. Hydrochloric acid or other suitable acid can be used to adjust the pH downward, and sodium bicarbonate, or other suitable base, can be used to adjust the pH upward.

To maintain the pH within the preferred range, in the frozen and thawed and reconstituted lyophilized pharmaceutical compositions the solution may be buffered with citrate or other suitable buffers. Citrate is the preferred buffer because it can maintain the pH of the solution without significant drug degradation. When using such buffers as phosphate, the pH cannot be maintained in the frozen state (See "Effect Of Freezing On The pH And Composition Of Sodium And Potassium Phosphate Solutions: The reciprocal system $KH_2PO_4$—$Na_2HPO_4$—$H_2O$," L. Van den Berg and D. Rose, Arch. Biochem. Biophys., 81, p. 319 (1959)). The addition of a buffer is desired for controlling the pH to enhance stability. Preferably, a suitable amount of sodium citrate used to buffer the formulation, controls the pH for maximum stability without significantly catalyzing or degrading the drug, or causing pain to the patient upon infusion.

Sodium citrate dihydrate also known as trisodium citrate dihydrate is the preferred form for the buffer used in the present invention. The amount of sodium citrate dihydrate is preferably within the range of about 0.25 to about 5 mg/ml, more preferably within the range of about 0.6 to about 5 mg/ml, and most preferably within the range of about 1.0 to about 4.0 mg/ml or any range or subcombination of ranges therein. Ranges are for reconstituted and diluted or thawed for administration.

As used herein citrate is citric acid or salts thereof, preferably sodium citrate. Sodium citrate includes: trisodium citrate anhydrous, trisodium citrate dihydrate, sodium citrate dihydrate and trisodium citrate pentahydrate. Sodium citrate dihydrate is also know as trisodium citrate dihydrate and is preferred.

Physiologically acceptable diluents may optionally be added to improve cake characteristics of lyophilized products. Acceptable diluents include but are not limited to sugars, inorganic salts and amino acids. Representative examples of acceptable sugars include dextrose, mannitol, lactose, and sucrose and the like. Representative examples of salts include sodium chloride, sodium phosphate, and calcium chloride and the like. Representative examples of acceptable amino acids include arginine, tyrosine, and leucine, and the like.

It may optionally be desirable to preferably add dextrose to the solution upon thawing the pharmaceutical composition or to the reconstituted lyophilized pharmaceutical composition to render the solution physiologically isosmotic (approximately 300 mOsmol/kg). Dextrose hydrous or anhydrous can be used in the present invention. The concentration of the dextrose hydrous is within the preferred range of about 5 to about 30 mg/ml, and more preferably within the range of about 6 to about 22 mg/ml or any combination or subcombination or ranges therein. After complete formulation and mixing, the premixed piperacillin or piperacillin/tazobactam solution further containing the particulate formation inhibitor is placed into suitable dosage containers. Suitable containers include those sold by Baxter under the trade name GALAXY®. The containers are then stored in a freezer at −20° C. or lower.

Typical pharmaceutical compositions of the invention include the following ranges:

Piperacillin in the range of about 8 mg/ml to about 500 mg/ml; more preferably about 12 mg/ml to about 300 mg/ml;

Tazobactam in the range of about 0.1 mg/ml to about 125 mg/ml; more preferably about 1.5 mg/ml to about 75 mg/ml;

Citrate in the range of about 0.25 mg/ml to about 25 mg/ml; more preferably about 0.6 mg/ml to about 15 mg/ml;

Particulate formation inhibitor in the range of about 0.002 mg/ml to about 10 mg/ml; more preferably about 0.003 to about 1 mg/ml;

Optionally added to pharmaceutical compositions of the invention is dextrose in the range of about 5 mg/ml to about 100 mg/ml.

Optionally added to pharmaceutical compositions of the invention are aminoglycosides in the range of about 0.1 mg/ml to about 75 mg/ml. A non-limiting example of a pharmaceutical composition of the invention, preferably in the case of a frozen composition, contains (a) piperacillin or a pharmaceutically acceptable salt thereof in an amount of about 4.0 g calculated as piperacillin free acid, (b) tazobactam or a pharmaceutically acceptable salt thereof in an amount of about 0.5 g calculated as tazobactam free acid, (c) about 1 mg of EDTA or of a pharmaceutically acceptable salt of EDTA and (d) about 100 ml of water for injection. The composition may contain as optional further ingredients about 0.2 g of citrate as buffer, about 2.0 g of dextrose, about 500 mg amikacin, or about 160 mg of tobramycin. The composition preferably includes (a) piperacillin sodium equivalent to about 4 g piperacillin free acid, (b) tazobactam sodium equivalent to about 0.5 g of tazobactam free acid and (c) substantially 1 mg of a sodium salt of EDTA and may include about 0.2 g of sodium citrate as buffer.

Optionally, the particulate formation inhibitor may be added before freezing or after thawing. Further, an aminoglycoside may optionally be added before freezing or after thawing, in particular, for use in a hospital setting.

Before use the frozen containers should be thawed in a conventional manner. The formulations will remain viable at room temperature for one day after removal from the freezer. Alternatively, the containers may be refrigerated at about 5° (±3° C.) for as much as 14 days.

Optionally added aminoglycosides to both the lyophilized and reconstituted and frozen and thawed specifically for administration to a patient include amikacin and tobramycin in a range of about 0.1 to about 75 mg/ml, in a preferred range of about 0.1 to about 15 mg/ml and more preferred in a range of about 1 to about 10 mg/ml.

Illustrative, non-limiting examples of the present formulations are set forth in TABLE 1 below. Numerous other examples can readily be envisioned in light of the guiding principles and teachings contained herein. For example, the solution pH could be varied and the dextrose may optionally be added and the concentration can be varied slightly and still allow the formulation to be isosmotic and the citrate buffer concentration can be varied, but retain sufficient buffer capacity without causing pain on infusion to the patient. It is apparent to those skilled in the art that the order of addition of the various components of the pharmaceutical composition of the invention may be varied. Further, that the examples given herein are intended to illustrate the invention and not in any sense to limit the manner in which the invention can be practiced.

The term, "lyophilized composition(s)" refers to the solid freeze-dried composition of matter prepared by the process of this invention and comprising as essential ingredients: (1) piperacillin; (2) tazobactam; further including (3) citrate and additionally including (4) a particulate formation inhibitor which further includes adjustment of the pH and optionally the addition of an aminoglycoside.

Optionally, added aminoglycosides, including amikacin in a lyophilized composition are present in a preferred range of about 1 to about 100 mg/ml and more preferred in a range of about 5 to about 75 mg/ml.

As is known to those skilled in the art, lyophilization is a process of drying in which water is sublimed from the product after it is frozen, by optionally applying a vacuum. Specifics of lyophilizing or freeze-drying are described in Remington's Pharmaceutical Sciences, Chapter 84, page 1565, 18$^{th}$ Edition, A. R. Gennaro, Editor, 1990, Mack Publishing Company.

Also, known to those skilled in the art are techniques other than lyophilization which may also be used. Non-limiting techniques to make the composition include: sterile powder filling of the components, singly, or as a complete blend. Non-limiting techniques to prepare the powder prior to filling include: spray drying, tray drying, bulk lyophilization, sizing process including milling and/or screening and precipitation.

Method of Making the Lyophilized Compositions of the Invention:

The lyophilized compositions of the present invention refer to a preparation prepared by freeze-drying a solution containing Zosyn®. The solution containing all of the ingredients, which include, piperacillin, and tazobactam, and further including citrate, and additionally including a particulate formation inhibitor and optionally an aminoglycoside at a suitable pH are frozen, optionally being subjected to a heat treating process to improve cake characteristics, and then being dried in a high vacuum for sublimating water. Such lyophilized preparations include lyophilized preparations for intravenous administration as mentioned above. The lyophilized preparation may be produced by conventional methods including tray lyophilization, and vial lyophilization methods. Vial lyophilization is advantageous for preparing multi-dosage units of the invention as described, infra. A powdered form may be prepared directly by other techniques such as spray drying, or blending of dry powders of the appropriate salts of the individual or combined ingredients.

In order to obtain a solution of the pharmaceutical compositions of the invention by the process of the present invention, sodium citrate dihydrate is dissolved in a suitable amount of a solvent and mixed and stirred. Piperacillin acid and Tazobactam acid are added and stirring continued. The solution is neutralized with a sufficient quantity of sodium bicarbonate, to reach a pH of about 6.5 and the EDTA (particularly edetate disodium) is added to the aqueous solution followed by the optional addition of an aminoglycoside. The solvent, standard solutions for injection or diluent are preferably an aqueous solvent such as water, purified water, water for injection, 5% dextrose in water or isotonic sodium chloride solution.

If desired, the processing solution before lyophilization may be subjected to a filtration process. The filtration process includes, for example in the case of injection preparations, a sterilizing filtration and/or an ultra filtration of the processing solution before lyophilization to eliminate microorganisms or other contaminating matter from the processing solution before lyophilization.

If desired, the processing solution before lyophilization may be subjected to a distributing process. The distributing process includes, for example in the case of vial lyophilizations, a process distributing a suitable volume of the processing solution before lyophilization into vials taking the concentration of piperacillin sodium/tazobactam sodium, citrate, particulate formation inhibitor and optionally an aminoglycoside into consideration in order that vial products carry a desired amount of piperacillin sodium/tazobactam sodium.

A lyophilization process is performed as follows:

Preferably, the lyophilized composition is prepared by a controlled freeze-drying process. The processing solution is first frozen, then subjected to a low pressure environment (a.k.a. vacuum) to facilitate sublimation, and gently heated to optimize the drying rate of the product.

A typical process for preparing a lyophilized composition comprises the sequential steps of:

(a) dissolving lyophilized composition ingredients comprising: Sodium Citrate Dihydrate, EDTA or other particulate formation inhibitor, Piperacillin Acid, Tazobactam Acid and optionally an aminoglycoside in an aqueous solvent; then adjusting pH to about 6.5;

(b) cooling the processing solution of step (a) to a temperature below −35° C.;

(c) evacuating the lyophilizer to a pressure of about 300 uM Hg (40 pascals) or less;

(d) heating of the product in the lyophilizer on a shelf set to about +5° C.;

(e) maintaining these conditions, under subatmospheric pressure for a time sufficient to remove water from the aqueous solvent and yield a solid lyophilized product.

(f) drying at about +45° C.

Preferably, step (a) is conducted by dissolving in an aqueous solvent. Moreover, step (b) is performed for a time period of approximately 4 hours, and (e) is preferably conducted for a period of at about 35 hours and step (f) is performed at a subatmospheric pressure less than about (300 milliTorr) (40 pascals) and those conditions are maintained for 10 hours after the 45° C. shelf temperature has been achieved.

The lyophilization process removes most of the water originally present, but the final product lyophilized composition may contain some free water. Typically, the water content can range from about 0% to about 2% weight percent. More typically, the water content ranges from about 0% to about 1%.

Dose-concentrate and Unit Dosage Configurations of the Invention:

A dose-concentrate configuration of the pharmaceutical composition of the invention is a sealed container holding an amount of the lyophilized pharmaceutical composition of the invention to be employed over a standard treatment interval such as 7 days. The dose-concentrate configuration is prepared by placing the lyophilized composition in a container (e.g., glass or plastic bottles, vials, ampoules) in sufficient amount to treat a mammal for a period ranging from 12 hours to 1 week, but preferably from 12 hours to 24 hours. The container preferably also contains an empty space of sufficient size to permit (i) addition of aqueous solvent plus (ii) additional space as necessary to permit agitation and effect complete solution of the lyophilized composition in the added aqueous solvent. The container may be equipped with a penetrable top, for example, a rubber seal, so that aqueous solvent may be added by penetrating the seal with a hypodermic syringe and the concentrate subsequently removed by the same means.

An example of a dose-concentrate configuration is a glass vial having a capacity of from about 250 to about 1000 milliliters containing about 25,000 to about 40,500 milligrams of lyophilized pharmaceutical composition of the invention.

A non-limiting specific example of an individual use configuration, is a 50 mL glass bottle with a rubber seal having a lyophilized pharmaceutical composition containing about 4000 mg of piperacillin sodium, about 200 mg of sodium citrate, about 500 mg of tazobactam sodium and about 1 mg of EDTA (particularly as a sodium salt). The empty space above the solid composition has ample room for addition of a solvent or diluent such as sterile water for injection plus room to agitate the total contents.

A further non-limiting specific example of a useable configuration, is an approximately 100 ml glass bottle with a rubber seal having a lyophilized pharmaceutical composition containing about 40.5 g of piperacillin sodium, about 1.8 g of sodium citrate, about 4.5 g of tazobactam sodium and about 9 mg of EDTA (particularly as a sodium salt). The empty space above the solid composition has ample room for addition of a solvent or diluent.

An additional non-limiting specific example of a useable configuration, in an appropriately sized glass bottle with a rubber seal having a lyophilized pharmaceutical composition containing about 2000 mg of piperacillin sodium, about 100 mg of sodium citrate, about 250 mg of tazobactam sodium and about 0.5 mg of EDTA (particularly as a sodium salt). The empty space above the solid composition has ample room for addition of a solvent or diluent such as sterile water for injection plus room to agitate the total contents.

The addition of the aqueous solvent to the dose-concentrate configuration results in a liquid concentrate which may then be conveniently used to form unit dosages of liquid pharmaceutical formulations by removing aliquot portions or entire contents for dilution as set out in the following section.

Unit Dose of the Invention:

The concentrated solution of lyophilized composition formed in the dose-concentrate container is added to an IV (intravenous) container containing a suitable aqueous solvent. Useful solvents are standard solutions for injection as previously described (e.g., 5% dextrose or sterile water etc.). Typical unit dosage IV bags are conventional glass or plastic containers having inlet and outlet means and having standard (e.g., 50 ml, 100 ml and 150 ml) capacities. The concentrated solution of lyophilized pharmaceutical formulation of the invention is added to the unit dose IV bag in an amount to achieve a concentration of about 8 to about 90 mg of Zosyn® per ml and preferably from about 20 to about 80 mg per ml.

Without departing from the object and scope of the present invention, other pharmaceutically acceptable additive agents may be added to the lyophilized preparations of the present invention.

Experimental Methods

Methods:

Samples are prepared according to the compositions described in Table I. Zosyn® 4.5 g as a frozen bag is first thawed or reconstituted, as appropriate:

A typical frozen bag of contains upon thawing the following ingredients:
Piperacillin Sodium about 40 mg/ml;
Tazobactam Sodium about 5 mg/ml;
Dextrose Hydrous, USP about 20 mg/ml;
Sodium Citrate dihydrate about 2 mg/ml.

Frozen bags are thawed on laboratory bench top.

For samples containing EDTA, 1 ml of a 1.0-mg/ml aqueous solution of edetate disodium dihydrate is added to the 5% Dextrose Injection Solution, USP. The fluid is mixed with gentle inversions for about 1 minute, and then set aside for 2 additional minutes prior to reconstitution.

Zosyn® containing solutions, other than frozen bags, are prepared by reconstituting the lyophilized cake with a 20 ml portion of Dextrose 5% (water), transferring the resulting solution into the IV-bag through a 0.2 uM syringe filter, and then rinsing the vial with a second 20 ml portion of Dextrose 5% (water). The rinse liquid is also recovered and added to the IV bag through a 0.2 uM syringe filter. The fluid in the bag is mixed with gentle inversions for about 30 seconds.

The bags are labeled with identity and reconstitution time.

When added, aminoglycosides are added immediately. The fluid in the bag is mixed with gentle inversions for about 30 seconds.

A 50 ml sample is drawn with a 60 cc syringe fitted with a 21-gauge needle.

A clean, particle free vial is rinsed with water for injection, and then filled with about 45 ml of the sample. HIAC testing is performed immediately.

Into a suitably sized sample vial, a 3 ml sample is prepared for HPLC testing. HPLC testing is begun within an hour of sample preparation (Table 1).

The remainder of the Zosyn® admixture samples (about 50 ml) are stored in a closed cabinet in the laboratory, at ambient temperature and tested again 24 hours later (Table 1).

Light obscuration testing is performed using a HIAC-3000. A testing method, based on USP 788 is followed for the analysis. (See TABLE I) The data is reported on a particle per ml basis. Particle results were based on the average of the second and third of 3 readings. The same sample was resampled and analyzed 24 hours after the first test. A summary of the HIAC data is provided as Table I.

Potency analysis is performed using a high pressure liquid chromatography (HPLC). The strength method for piperacillin can be obtained in USP-26 (2003) pages 1483–1485. HPLC analysis was preformed initially and after 24 hours on each sample generated. A summary of the HPLC data is provided as Table I.

Materials:
1. Zosyn® 4.5 g lyophilized vials, Experimental Lot, provided by Technical Services, Lederle Piperacillin, Carolina, PR.
2. Zosyn® with Citrate, 4.5 g lyophilized vials, Experimental Lot, provided by Technical Services, Lederle Piperacillin, Carolina, PR.
3. Zosyn® Frozen IV bags (containing Citrate), Baxter
4. Amikacin Sulfate Injection, USP, 500 mg/2 ml (Bedford Laboratories) (total of 500 mg used per bag)
5. Tobramycin Sulfate Injection, USP, 80 mg/2 ml (Apothecon) (total of 160 mg used per bag)
6. 5% Dextrose Injection, USP. (B. Braun)

Atypical lyophilized vial contains:
Piperacillin sodium about 4000 mg; and
Tazobactam Sodium about 500 mg.

The following TABLE I has been divided into different sections (SUBTABLE IA, SUBTABLE IB, SUBTABLE IC, SUBTABLE ID AND SUBTABLE IE). Results shown in the same SUBTABLE represent experiments carried out on the same day with the same batch of Zosyn® containing solution.

TABLE I

DESCRIPTION OF EXPERIMENTAL SAMPLES

| Solution*** | Aminoglycoside mg/ml | Zinc Level Solution[a] | EDTA* mg/ml | Piperacillin Assay | | | Particulate Counts per mL | | | |
|---|---|---|---|---|---|---|---|---|---|---|
| | | | | Initial Assay mg/ml | 24 Hour mg/ml | % Remaining Based on initial | Time Zero 10 μm | 25 μm | Time 24 10 μm | 25 μm |
| SUBTABLE IA | | | | | | | | | | |
| 1 | | 0.08 | | 37.09 | 39.19 | 105.66** | 19 | 0 | 55 | 2 |
| 1 | | 0.08 | 0.01 | 39.67 | 39.27 | 98.99 | 11 | 1 | 9 | 0 |
| SUBTABLE IB | | | | | | | | | | |
| 1 | | 0.59 | | 36.19 | 39.90 | 110.34** | 18 | 0 | 76 | 2 |
| 1 | | 0.59 | 0.01 | 40.28 | 39.62 | 98.36 | 8 | 1 | 22 | 0 |
| 1 | T (1.6) | 0.59 | | 39.13 | 36.74 | 93.89 | 65 | 4 | 1247 | 9 |
| 1 | A (5.0) | 0.59 | | 39.58 | 38.74 | 97.88 | 9 | 0 | 128 | 3 |
| SUBTABLE IC | | | | | | | | | | |
| 2 | | 0.01 | | 46.81 | 45.54 | 97.29 | 10 | 3 | 189 | 2 |
| 2 | | 0.01 | | 47.13 | 44.88 | 95.23 | 13 | 1 | 117 | 1 |
| 2 | | 0.01 | 0.01 | 39.50 | 39.93 | 101.09 | 34 | 0 | 29 | 0 |
| 2 | T (1.6) | 0.01 | | 43.07 | 40.10 | 93.10 | 12 | 1 | 57 | 2 |
| 2 | A (5.0) | 0.01 | | 43.70 | 42.09 | 96.32 | 23 | 1 | 159 | 6 |
| SUBTABLE ID | | | | | | | | | | |
| 3 | | 0.59 | | 40.09 | 39.37 | 98.20 | 4 | 0 | 18 | 0 |
| 3 | | 0.59 | 0.01 | 39.93 | 39.58 | 99.12 | 6 | 0 | 7 | 0 |
| 3 | A (5.0) | 0.59 | | 39.80 | 38.52 | 96.78 | 15 | 0 | 74 | 1 |
| 3 | A (5.0) | 0.59 | 0.01 | 38.17 | 36.90 | 96.67 | 10 | 0 | 21 | 1 |
| SUBTABLE IE | | | | | | | | | | |
| 3 | | 0.08 | | 39.48 | 39.05 | 98.91 | 8 | 0 | 17 | 0 |
| 3 | | 0.08 | 0.01 | 39.03 | 39.29 | 100.67 | 2 | 0 | 29 | 0 |
| 3 | A (5.0) | 0.08 | | 39.76 | 37.82 | 95.12 | | | 44 | 2 |
| 3 | T (1.6) | 0.08 | 0.01 | 39.50 | 39.93 | 101.09 | 61 | 3 | 267 | 3 |

***4.5 Zosyn ®, Zosyn ®/Citrate or Zosyn ® Frozen Solution
**Incomplete mixing of sample
*(edetate disodium dihydrate)
1. Zosyn ®
2. Zosyn ®/Citrate Frozen
3. Zosyn ®/Citrate Lyophilized Reconstituted
[a]Parts Per Million, an average of two tests
T = tobramycin and A = amikacin Typical Preparation of 200 liter (approximately 11,800 units) Formula:

| Ingredient | mg/vial | kilos |
|---|---|---|
| piperacillin monohydrate | 400 | 47.374 |
| tazobactam | 500 | 5.922 |
| sodium citrate dihydrate | 200 | 2.369 |
| edetate disodium (dihydrate) USP | 1 | 0.012 |
| sodium bicarbonate, USP | qs. | pH to 6.5 target |
| water for injection, USP | qs. | 200 liters |

Typical Process for Preparation of Bulk solution Comprising Steps of:
Preparation of Solution A
a) In a suitable stainless steel processing vessel is added 15 liters of water for injection USP.
b) While stirring with a properly,sized impeller-type mixer the following ingredients are added:
Sodium Citrate, Dihydrate; and
Edetate Disodium, USP;
Mixing is continued until a clear solution is obtained (SOLUTION A).

Preparation of Solution B
a) In a suitable stainless steel processing vessel (properly sized to contain and mix 200 liters) 140 liters of water for injection is added while stirring with a properly sized impeller-type mixer add the following ingredients:
Piperacillin Monohydrate;
Tazobactam; and
SOLUTION A
b) Adjust pH to 6.5 with sodium Bicarbonate, USP;
c) Optionally adding an aminoglycoside;
d) Adjust volume to 200 liters with additional water for injection, USP to give a bulk solution.

Process for Lyophilization:
a) The bulk solution is optionally passed through a 0.2 uM filter;
b) Approximately 16.9 ml are filled into each suitable lyophilization vial;
c) Each vial is fitted with a suitable lyophilization stopper, inserted approximately half way to facilitate venting of water vapor;
d) Vials are loaded on a lyophilizer shelf prechilled to 5° C.;
e) Vials are frozen to a temperature below −35° C., and held for 4 hours;
f) The lyophilizer is evacuated to a pressure not exceeding 300 uM Hg (micrometers of mercury) (40 pascals);
g) Shelf temperature is gradually raised to 5° C.;

h) The 5° C. shelf temperature is maintained for about 30 hours;
i) Shelf temperature is then increased to 45° C. over a period of 18 hours;
j) The 45° C. shelf temperature is maintained for 10 hours;
k) Shelf temperature is reduced to 30° C., and maintained for 1 hour;
l) The chamber is repressurized, and vials are stoppered.

What is claimed is:

1. A pharmaceutical composition comprising effective amounts of (a) piperacillin or a pharmaceutically acceptable salt thereof, (b) tazobactam or a pharmaceutically acceptable salt thereof and, (c) as a particulate formation inhibitor, an aminocarboxylic acid chelating agent or a pharmaceutically acceptable salt thereof.

2. A pharmaceutical composition according to claim 1 further comprising an effective amount of a buffer.

3. A pharmaceutical composition according to claim 1 wherein the piperacillin is piperacillin sodium.

4. A pharmaceutical composition according to claim 1 wherein the tazobactam is tazobactam sodium.

5. A pharmaceutical composition according to claim 1 wherein the particulate formation inhibitor is at least one compound selected from the group ethylenediaminetetraacetic acid (EDTA), diethylenetriaminepentaacetic acid (DTPA), hydroxyethylenediaminetriacetic acid (HEDTA), nitrilotriacetic acid (NTA), and the pharmaceutically acceptable salts thereof.

6. A pharmaceutical composition according to claim 5 wherein the particulate formation inhibitor is EDTA.

7. A pharmaceutical composition according to claim 2 wherein the buffer is citrate.

8. A pharmaceutical composition according to claim 7 wherein the citrate is sodium citrate.

9. A pharmaceutical composition according to claim 1 further comprising an aminoglycoside.

10. A pharmaceutical composition according to claim 9 wherein the aminoglycoside is selected from amikacin and tobramycin.

11. A pharmaceutical composition according to claim 10 wherein the aminoglycoside is amikacin.

12. A pharmaceutical composition according to claim 10 wherein the aminoglycoside is tobramycin.

13. A pharmaceutical composition according to claim 2 further comprising an aminoglycoside.

14. A pharmaceutical composition according to claim 13 wherein the aminoglycoside is selected from amikacin and tobramycin.

15. A pharmaceutical composition according to claim 14 wherein the aminoglycoside is amikacin.

16. A pharmaceutical composition according to claim 15 wherein the aminoglycoside is tobramycin.

17. A pharmaceutical composition according to claim 2 wherein the effective amount of buffer maintains the pH at about 6.0 to about 7.5.

18. A pharmaceutical composition according to claim 17 wherein the pH is about 6.5.

19. A pharmaceutical composition according to claim 1 wherein the composition is a powder.

20. A pharmaceutical composition according to claim 2 wherein the composition is a powder.

21. A pharmaceutical composition of claim 1 wherein the composition is a solution and the piperacillin is present in an amount from about 8 mg/ml to about 500 mg/ml.

22. A pharmaceutical composition of claim 8 wherein the composition is a solution and the sodium citrate buffer is present in an amount from about 0.25 mg/ml to about 25 mg/ml.

23. A pharmaceutical composition according to claim 1 wherein the composition is a solution and the tazobactam is present in an amount from about 0.1 mg/ml to about 125 mg/ml.

24. A pharmaceutical composition according to claim 1 wherein the composition is a solution, said composition further comprising an effective amount of dextrose to render the composition physiologically isosmotic.

25. A pharmaceutical composition according to claim 24 wherein the effective amount of dextrose is from about 5 mg/ml to about 100 mg/ml.

26. A pharmaceutical composition according to claim 15 wherein the composition is a solution and amikacin is present in an amount of about 0.1 mg/ml to about 75 mg/ml.

27. A pharmaceutical composition according to claim 16 wherein the composition is a solution and tobramycin is present in an amount of about 0.1 mg/ml to about 75 mg/ml.

28. A pharmaceutical composition according to claim 11 wherein the composition is a solution and amikacin is present in an amount of about 0.1 mg/ml to about 75 mg/ml.

29. A pharmaceutical composition according to claim 12 wherein the composition is a solution and tobramycin is present in an amount of about 0.1 mg/ml to about 75 mg/ml.

30. A pharmaceutical composition according to claim 6 wherein the composition is a solution and EDTA is present in an amount of about 0.002 mg/ml to about 10 mg/ml.

31. A pharmaceutical composition according to claim 30 wherein the EDTA is present in an amount of about 0.003 mg/ml to about 1 mg/ml.

32. A pharmaceutical composition according to claim 1 wherein said pharmaceutical composition is a dose concentrate in a sealed container wherein said container has a space sufficient for introduction of a volume of aqueous solvent sufficient to form a concentrated solution of said pharmaceutical composition.

33. A pharmaceutical composition according to claim 2 wherein said pharmaceutical composition is a dose concentrate in a sealed container wherein said container has a space sufficient for introduction of a volume of aqueous solvent sufficient to form a concentrated solution of said pharmaceutical composition.

34. A pharmaceutical composition according to claim 1 wherein said pharmaceutical composition is a solution and is a unit dose contained in an IV bag or IV bottle for intravenous administration.

35. A pharmaceutical composition according to claim 2 wherein said pharmaceutical composition is a solution and is a unit dose contained in an IV bag or IV bottle for intravenous administration.

36. A pharmaceutical composition comprising (a) piperacillin or a pharmaceutically acceptable salt thereof in an amount of about 4.0 g calculated as piperacillin free acid, (b) tazobactam or a pharmaceutically acceptable salt thereof in an amount of about 0.5 g calculated as tazobactam free acid, (c) about 1 mg of EDTA or a pharmaceutically acceptable salt of EDTA and (d) water for injection.

37. A pharmaceutical composition according to claim 36 further comprising about 0.2 g of citrate.

38. A pharmaceutical composition according to claim 36 wherein (a) the piperacillin or a pharmaceutically acceptable salt is piperacillin sodium as about 4 g piperacillin free acid, (b) the tazobactam or a pharmaceutically acceptable salt is tazobactam sodium as about 0.5 g of tazobactam free acid, (c) about 1 mg of a sodium salt of EDTA and (d) about 100 ml of water for injection.

39. A pharmaceutical composition according to claim 38 further comprising about 0.2 g of sodium citrate.

40. A pharmaceutical composition according to claim 36, further comprising about 2.0 g of dextrose.

41. A pharmaceutical composition according to claim 36 further comprising an aminoglycoside.

42. A pharmaceutical composition according to claim 41, wherein the aminoglycoside is amikacin and is present in an amount of about 500 mg.

43. A pharmaceutical composition according to claim 41, wherein the aminoglycoside is tobramycin and is present in an amount of about 160 mg.

44. A pharmaceutical composition according to claim 36 wherein the amount of water for injection is 100 ml.

45. A pharmaceutical composition according to claim 36 wherein said composition is frozen and capable of being thawed and, if desired, further diluted with a compatible diluent prior to administration to a mammal.

46. A pharmaceutical composition comprising (a) about 89% piperacillin or a pharmaceutically acceptable salt thereof, (b) about 11% tazobactam or a pharmaceutically acceptable salt thereof and, as a particulate formation inhibitor, about 0.02% of an aminocarboxylic acid chelating agent or a pharmaceutically acceptable salt thereof.

47. A pharmaceutical composition comprising (a) about 85% piperacillin or a pharmaceutically acceptable salt thereof, (b) about 11% tazobactam or a pharmaceutically acceptable salt thereof, (c) about 0.02% of an aminocarboxylic acid chelating agent or a pharmaceutically acceptable salt thereof as a particulate formation inhibitor, and about (d) 4% of a buffer.

48. A pharmaceutical composition according to claim 47 wherein the aminocarboxylic acid chelating agent is EDTA.

49. A pharmaceutical composition according to claim 47 wherein the buffer is citrate.

50. A pharmaceutical composition according to claim 2 wherein the composition is a solution and the piperacillin sodium, tazobactam sodium, citrate as buffer and as particulate formation inhibitor an aminocarboxylic acid chelating agent are present in an amount from about 9 mg/ml to about 125 mg/ml.

51. A pharmaceutical composition according to claim 50 wherein the composition is a solution and the piperacillin sodium, tazobactam sodium, citrate as buffer and as particulate formation inhibitor an aminocarboxylic acid chelating agent are present in an amount from about 14 mg/ml to about 115 mg/ml.

52. A pharmaceutical composition according to claim 51 wherein the composition is a solution and the piperacillin sodium, tazobactam sodium, citrate as buffer and as particulate formation inhibitor an aminocarboxylic acid chelating agent are present in an amount from about 20 mg/ml to about 105 mg/ml.

53. A method for the treatment or control of bacterial infections in a mammal, said infections being caused by piperacillin/tazobactam susceptible bacteria wherein the method comprises administering to said mammal a therapeutically effective amount of the pharmaceutical composition of claim 1.

54. A method for the treatment or control of bacterial infections in a mammal, said infections being caused by piperacillin/tazobactam susceptible bacteria wherein the method comprises administering to said mammal a therapeutically effective amount of the pharmaceutical composition of claim 2.

55. A method for the treatment or control of bacterial infections in a mammal, said infections caused by piperacillin/tazobactam susceptible bacteria wherein the method comprises coadministering a pharmaceutical composition of claim 1 and an aminoglycoside.

56. The method according to claim 55 wherein the aminoglycoside is selected from amikacin and tobramycin.

57. The method according to claim 56 wherein the aminoglycoside is amikacin.

58. The method according to claim 56 wherein the aminoglycoside is tobramycin.

59. A method for the treatment or control of bacterial infections in a mammal, said infections caused by piperacillin/tazobactam susceptible bacteria wherein the method comprises coadministering a pharmaceutical composition of claim 2 and an aminoglycoside.

60. The method according to claim 59 wherein the aminoglycoside is selected from amikacin and tobramycin.

61. The method according to claim 60 wherein the aminoglycoside is amikacin.

62. The method according to claim 60 wherein the aminoglycoside is tobramycin.

63. A process for preparing a lyophilized pharmaceutical composition which comprises the steps of:
  a) dissolving sodium citrate dihydrate, EDTA, piperacillin, and tazobactam, in an aqueous solvent to form a solution and adjusting the pH of the solution to about 6.5;
  b) cooling the solution to a temperature below −35° C. in a lyophilizer;
  c) evacuating the lyophilizer to a pressure of about 300 μM Hg (40 pascals) or less;
  d) heating the lyophilizer to about +5° C.;
  e) maintaining the temperature and pressure for a sufficient time to remove water from the aqueous solvent to form a lyophilized solid;
  f) drying the lyophilized solid at about +45° C. to form a lyophilized composition.

64. The process according to claim 63 further comprising in a step a) dissolving an aminoglycoside with the sodium citrate dihydrate, EDTA, piperacillin and tazobactam.

65. The process according to claim 64 wherein the aminoglycoside is selected from amikacin and tobramycin.

66. The process according to claim 65 wherein the aminoglycoside is amikacin.

67. The process according to claim 65 wherein the aminoglycoside is tobramycin.

68. A process of making a reconstitutable pharmaceutical composition which comprises the steps of:
  a) dissolving sodium citrate dihydrate, EDTA, piperacillin, and tazobactam, in an aqueous solvent to form a solution and adjusting the pH of the solution to about 6.5;
  b) cooling the solution to a temperature below −35° C. in a lyophilizer;
  g) evacuating the lyophilizer to a pressure of about 300 μM Hg (40 pascals) or less;
  h) heating the lyophilizer to about +5° C.;
  i) maintaining the temperature and pressure for a sufficient time to remove water from the aqueous solvent to form a lyophilized solid;
  j) drying the lyophilized solid at about +45° C. to form the reconstitutable pharmaceutical composition.

69. The process according to claim 68 further comprising in step a) dissolving an aminoglycoside with the sodium citrate dihydrate, EDTA, piperacillin and tazobactam wherein the aminoglycoside is amikacin and the amikacin is present in an amount of about 0.1 mg/ml to about 75 mg/ml of the reconstitutable pharmaceutical composition.

70. The process according to claim 68 further comprising in step a) dissolving an aminoglycoside with the sodium citrate dihydrate, EDTA, piperacillin and tazobactam wherein the aminoglycoside is tobramycin and the tobramycin is present in an amount of about 0.1 mg/ml to about 75 mg/ml of the reconstitutable pharmaceutical composition.

71. The process according to claim 68 wherein the EDTA in the composition is present in an amount of about 0.002 mg/ml to about 10 mg/ml.

72. The process according to claim 71 wherein the EDTA is present in an amount of about 0.003 mg/ml to about 1 mg/ml.

73. A process for preparing a pharmaceutical composition which comprises the steps of:
  a) dissolving an effective amount of sodium citrate dihydrate in an aqueous solvent to form a solution;

b) adding effective amounts of piperacillin, and tazobactam;

c) adjusting the pH to about 6 5; and d) adding an effective amount of EDTA.

74. The process according to claim 73 further comprising in step b) adding an effective amount of an aminoglycoside with the effective amounts of piperacillin and tazobactam.

75. The process according to claim 74 wherein the aminoglycoside is selected from amikacin and tobramycin.

76. The process according to claim 75 wherein the aminoglycoside is amikacin.

77. The process according to claim 76 wherein the amikacin is present in an amount of about 0.1 mg/ml to about 75 mg/ml.

78. The process according to claim 75 wherein the aminoglycoside is tobramycin.

79. The process according to claim 78 wherein the tobramycin is present in an amount of about 0.1 mg/ml to about 75 mg/ml.

80. The process according to claim 73 wherein the EDTA is present in an amount of about 0.002 mg/ml to about 10 mg/ml.

81. The process according to claim 80 wherein the EDTA is present in an amount of about 0.003 mg/ml to about 1 mg/ml.

82. A process for the manufacture of a reconstitutable pharmaceutical composition in the form of a powder which process comprises the steps of:

dissolving effective amounts of (a) piperacillin or a pharmaceutically acceptable salt thereof, tazobactam or a pharmaceutically acceptable salt thereof and, as a particulate formation inhibitor, an aminocarboxylic acid chelating agent or a pharmaceutically acceptable salt thereof in an aqueous solvent to form a solution, (b) adjusting the pH of said solution in the range of about 6.0 to about 7.5 and (c) freeze drying said solution to form a reconstitutable powder.

83. The process according to claim 82 further comprising in step a) dissolving an aminoglycoside with the piperacillin, tazobactam and particulate formation inhibitor.

84. The process according to claim 83 wherein the aminoglycoside is selected from amikacin and tobramycin.

85. The process according to claim 84 wherein the aminoglycoside is amikacin.

86. The process according to claim 84 wherein the aminoglycoside is tobramycin.

87. The process according to claim 82 wherein in step b the pH is adjusted to about 6.5 with an effective amount of a buffer.

88. The process according to claim 87 wherein the buffer is citrate.

89. The process according to claim 88 wherein the citrate is sodium citrate.

90. The process according to claim 73 further comprising step e) freezing or lyophilizing to form the composition.

* * * * *

UNITED STATES PATENT AND TRADEMARK OFFICE
CERTIFICATE OF CORRECTION

PATENT NO. : 6,900,184 B2
DATED : May 31, 2005
INVENTOR(S) : Jonathan Marc Cohen et al.

It is certified that error appears in the above-identified patent and that said Letters Patent is hereby corrected as shown below:

Title page,
Item [56], References Cited, U.S. PATENT DOCUMENTS, delete "2002/0035061 A1 3/2002    Krieger et al." and insert -- 2002/035061 A1 3/2002 Krieger et al. --.
Item [57], ABSTRACT,
Line 1, delete "piperacillin with tazobactam" and insert -- (piperacillin with tazobactam) --.

Signed and Sealed this

Twenty-third Day of August, 2005

JON W. DUDAS
*Director of the United States Patent and Trademark Office*